US007421300B2

(12) United States Patent
Smits

(10) Patent No.: US 7,421,300 B2
(45) Date of Patent: Sep. 2, 2008

(54) IMPLANTATION OF MEDICAL DEVICE WITH MEASUREMENT OF BODY SURFACE POTENTIAL

(75) Inventor: Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 424 days.

(21) Appl. No.: 11/263,101

(22) Filed: Oct. 31, 2005

(65) Prior Publication Data

US 2007/0100382 A1 May 3, 2007

(51) Int. Cl.
*A61N 1/05* (2006.01)
(52) U.S. Cl. .................. 607/119; 600/424; 600/393; 607/5; 606/129
(58) Field of Classification Search ............ 607/5, 607/119, 122, 129; 600/393, 508, 512, 509, 600/424; 606/129, 130; 128/898
See application file for complete search history.

(56) References Cited

U.S. PATENT DOCUMENTS

| 4,374,382 | A | 2/1983 | Markowitz |
|---|---|---|---|
| 4,974,598 | A | 12/1990 | John |
| 5,105,809 | A | 4/1992 | Bach, Jr. et al. |
| 5,117,824 | A | 6/1992 | Keimel et al. |
| 5,193,535 | A | 3/1993 | Bardy et al. |
| 5,311,873 | A | 5/1994 | Savard et al. |
| 5,346,506 | A | 9/1994 | Mower et al. |
| 5,483,968 | A | 1/1996 | Adam et al. |
| 5,531,770 | A | 7/1996 | Kroll et al. |
| 5,545,186 | A | 8/1996 | Olson et al. |
| 5,564,422 | A | 10/1996 | Chen et al. |
| 5,692,515 | A | 12/1997 | Rahn et al. |
| 5,954,753 | A | 9/1999 | Alt et al. |
| 6,050,267 | A * | 4/2000 | Nardella et al. ............. 128/899 |
| 6,067,473 | A | 5/2000 | Greeninger et al. |
| 6,345,200 | B1 | 2/2002 | Mouchawar et al. |
| 2002/0052631 | A1 | 5/2002 | Sullivan et al. |
| 2002/0133206 | A1 | 9/2002 | Daum et al. |
| 2003/0083587 | A1 * | 5/2003 | Ferek-Petric ................ 600/512 |

* cited by examiner

*Primary Examiner*—Mark Bockelman
*Assistant Examiner*—Roland Dinga
(74) *Attorney, Agent, or Firm*—Daniel G. Chapik

(57) ABSTRACT

Methods of implanting at least one lead for a cardio defibrillator using body surface potential (BSP) electrodes are disclosed. The methods may include installing defibrillation electrodes in a patient, attaching at least three BSP electrodes to the patient's skin, creating a potential difference between the defibrillation electrodes, and measuring the resulting body surface potential at the three BSP electrodes. Once the resulting BSP is measured, the methods may include determining the amplitude of a resultant vector formed by the measured BSP potential differences. The location of a defibrillation electrode may then be manipulated to increase the amplitude of the resultant vector formed by the measured BSP potential differences.

16 Claims, 4 Drawing Sheets

IMPLANTATION OF MEDICAL DEVICE WITH MEASUREMENT OF BODY SURFACE POTENTIAL

FIELD

Most of the embodiments of the disclosure relate generally to methods for implanting an implantable apparatus for treating cardiac arrhythmias, particularly ventricular fibrillation. More particularly, most of the embodiments relate to methods for implanting an implantable apparatus with predictable results based on body surface potential (BSP) measurements.

BACKGROUND

Implantable medical devices are available to provide therapies for restoring normal cardiac rhythms by delivering electrical shock therapy for cardioverting or defibrillating the heart, in addition to providing cardiac pacing. Such a device, commonly known as an implantable cardioverter defibrillator ("ICD") senses a patient's heart rhythm and may classify the rhythm according to a number of programmable rate zones in order to detect episodes of tachycardia or fibrillation. Single chamber devices are available for treating either atrial arrhythmias or ventricular arrhythmias, and dual chamber devices are available for treating both atrial and ventricular arrhythmias. Rate zone classifications may include slow tachycardia, fast tachycardia, and fibrillation.

Upon detecting an abnormal rhythm, the ICD may select and deliver a therapy based upon detected rate and/or other programmable criteria, for example. Cardiac pacing may be delivered in response to the absence of sensed intrinsic depolarizations within a specified time window, referred to as P-waves in the atrium and R-waves in the ventricle. In response to tachycardia detection, a number of tiered therapies may be delivered beginning with anti-tachycardia pacing therapies and possibly escalating to more aggressive therapies until the tachycardia is terminated. Termination of a tachycardia is commonly referred to as "cardioversion." Ventricular fibrillation (VF) is a serious life-threatening condition and is normally treated by delivering high-energy shock therapy. Termination of VF in this manner is normally referred to as "defibrillation."

In many available ICDs, a physician or operator has the ability to program particular anti-arrhythmia therapies into the device ahead of time, and a menu of therapy options is typically provided. For example, on initial detection of an atrial or ventricular tachycardia, an anti-tachycardia pacing therapy may be selected and delivered to the chamber or chambers in which the tachycardia is diagnosed. After the initial therapy is delivered, a subsequent redetection of tachycardia may lead to a more aggressive anti-tachycardia pacing therapy, for example. If repeated attempts at anti-tachycardia pacing therapies fail, a cardioversion or defibrillation shock may next be selected. For an overview of tachycardia detection and treatment therapies, reference is made to U.S. Pat. No. 5,545,186 issued to Olson et al.

The objectives of determining proper placement of a right ventricular coil electrode and a defibrillation threshold have been accomplished in the past by installing the right ventricular electrode in the patient's heart, inducing ventricular fibrillation, and trying to treat the defibrillation at various voltages and locations until the proper location for the right ventricular electrode and the defibrillation threshold are determined. The ventricular fibrillation may be induced by a pulsing of the right ventricular coil electrode synchronized with the T-wave, by passing an alternating current through the heart, or by other means known in the art. The patient is under general anesthesia or is sedated but conscious throughout this procedure, but it is still a potentially traumatic and painful procedure, since the typical defibrillation pulse is 750 volts and several attempts may be required to determine proper lead placement and defibrillation threshold.

SUMMARY

One embodiment of the present invention is directed toward a method of implanting at least one lead for a cardio defibrillator. The method includes the steps of installing a RV defibrillation electrode in a right ventricle of a patient's heart and installing a second defibrillation electrode in the patient. At least three BSP electrodes capable of measuring body surface potential are attached to the patient's skin. A potential difference between the RV defibrillation electrode and the second defibrillation electrode is created. The body surface potential at the at least three BSP electrodes caused by the potential difference between the defibrillation electrodes may be measured. From this, the amplitude of a resultant vector formed by the measured potential differences between the at least three BSP electrodes may be determined, the measured potential differences between the at least three BSP electrodes forming component vectors of the resultant vector. The location of at least one of the defibrillation electrodes may then be manipulated to increase the amplitude of the resultant vector formed by the measured potential differences between the at least three BSP electrodes.

Another embodiment of the invention includes a method of implanting at least one lead for a cardio defibrillator including the steps of installing a RV defibrillation electrode in a right ventricle of a patient's heart and installing a second and a third defibrillation electrode in the patient. At least three BSP electrodes capable of measuring body surface potential are attached to the patient's skin. A potential difference between the RV defibrillation electrode and the second defibrillation electrode may be created. The body surface potential at the at least three BSP electrodes caused by the potential difference between the defibrillation electrodes may be measured by means known in the art. The amplitude of a resultant vector formed by the measured potential differences between the at least three BSP electrodes may be determined, the measured potential differences between the at least three BSP electrodes forming component vectors of the resultant vector. The method may also include the step of creating a potential difference between the RV defibrillation electrode and the third defibrillation electrode to determine if such potential difference increases the amplitude of the resultant vector formed by the measured potential differences between the at least three BSP electrodes.

Yet another embodiment of the invention may include a method of implanting at least one lead for a cardio defibrillator including the steps of installing a RV defibrillation electrode in a right ventricle of a patient's heart and installing a second and a third defibrillation electrode in the patient. At least two BSP electrodes capable of measuring body surface potential may be attached to the patient's skin. A potential difference between the RV defibrillation electrode and the second defibrillation electrode may be created. The body surface potential at the at least two BSP electrodes caused by the potential difference between the defibrillation electrodes may be measured. The amplitude of a resultant vector formed by the measured potential differences between the at least two BSP electrodes may be determined, the measured potential differences between the at least two BSP electrodes forming at least one component vector of the resultant vector. The method may also include the steps of creating a potential difference between the RV defibrillation electrode and both the second and third defibrillation electrodes to determine if such potential difference increases the amplitude of the resultant vector formed by the measured potential differences between the at least two BSP electrodes.

DETAILED DESCRIPTION OF THE ILLUSTRATED EMBODIMENTS

Figure 1:
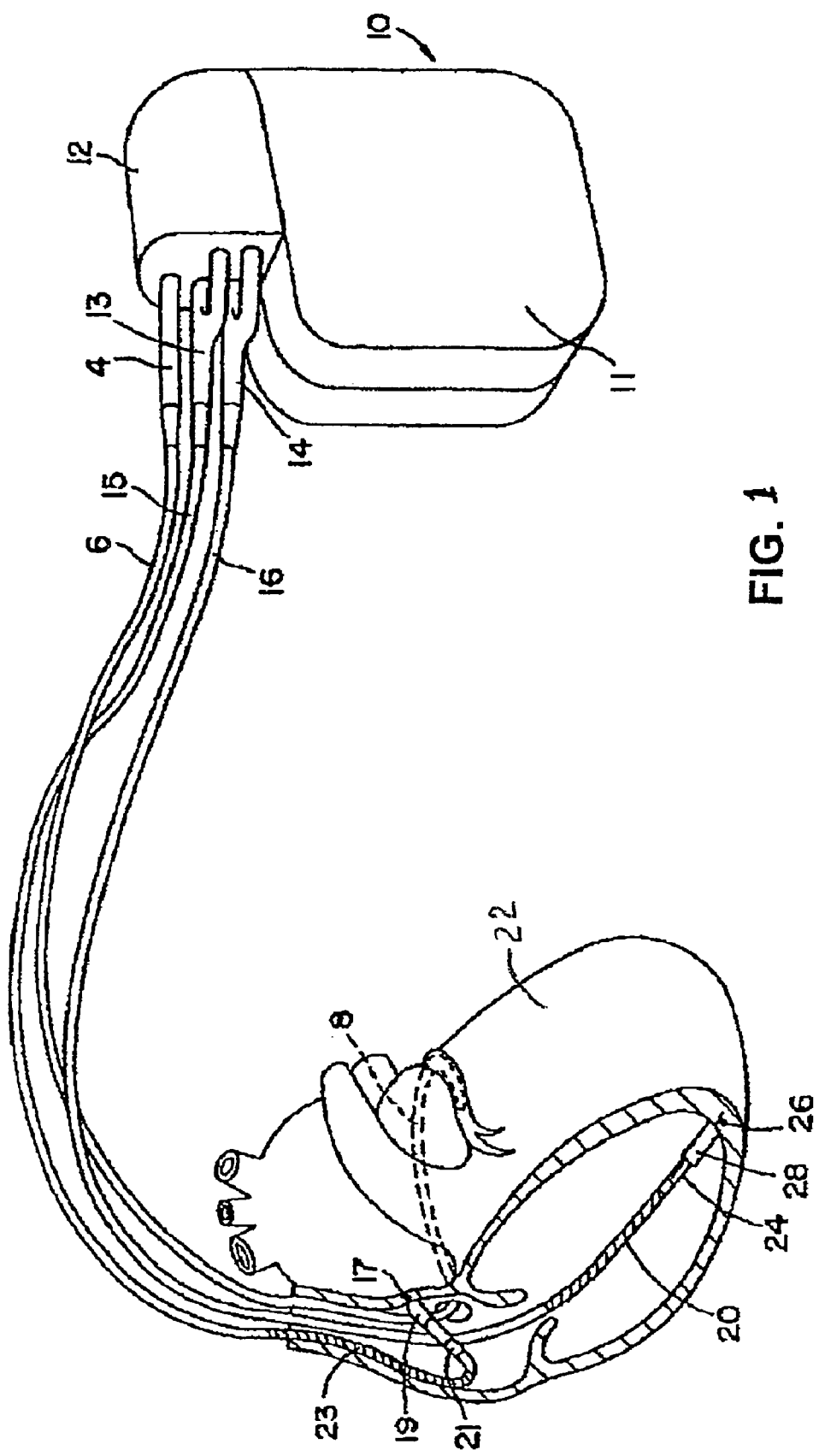
FIG. 1 is an illustration of an implantable cardiac stimulation device capable of pacing, cardioversion, and defibrillation in communication with a heart via stimulation and sensing leads.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the appended claims.

For purposes of illustration only, the invention is described below in the context of implantable cardioverter defibrillators ("ICDs"). However, embodiments of the invention are not limited to use with ICDs, and may be employed in conjunction with other types of implantable cardiac devices such as pacemakers, cardiac resynchronization therapy (CRT) devices, implantable recording devices, and similar systems.

An exemplary ICD 10 is shown in FIG. 1, with which methods included in the present invention may be used. The ICD 10 is shown coupled to a heart by way of leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 may be positioned such that its distal end is in the vicinity of the right atrium and the superior vena cava. Lead 15 may be equipped with a ring electrode 21 and an extendable helix electrode 17, mounted retractably within electrode head 19, for sensing and pacing in the right atrium. Lead 15 may be further equipped with a coil electrode 23 for delivering high-energy shock therapy. The ring electrode 21, the helix electrode 17 and the coil electrode 23 may each be connected to an insulated conductor within the body of the right atrial lead 15. Each insulated conductor is coupled at its proximal end to a connector carried by bifurcated connector 13.

A coronary sinus lead 6 may be advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 and 23 for defibrillation of the atria or ventricles. It is recognized that alternate lead systems may be substituted for the lead system illustrated in FIG. 1. While a particular multi-chamber ICD and lead system is illustrated in FIG. 1, methodologies included in the present invention may be adapted for use with any single chamber, dual chamber, or multichamber ICD or pacemaker system, or other cardiac monitoring device.

Figure 2:
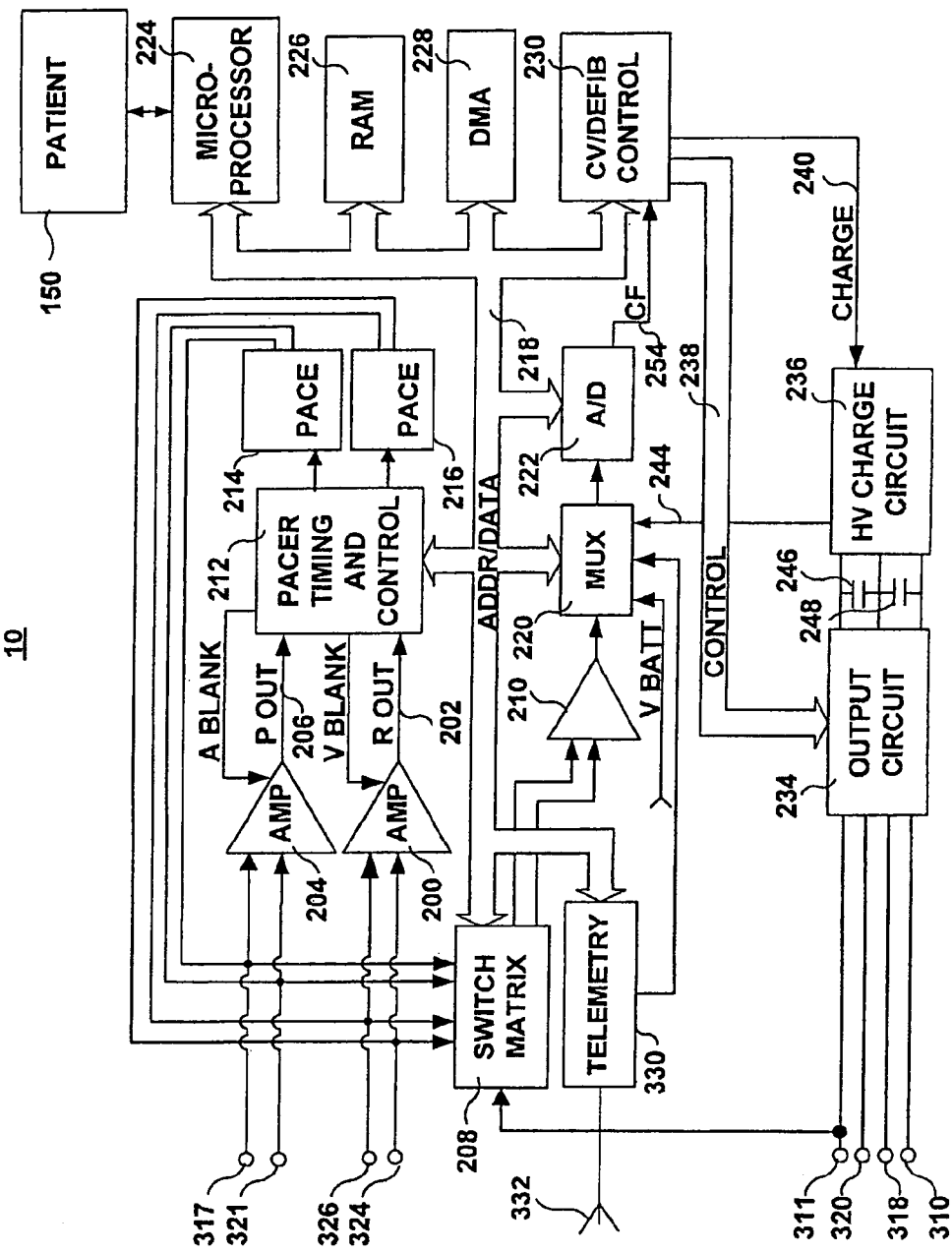
FIG. 2 is a functional schematic diagram of an ICD in accordance with embodiments of the invention.

A functional schematic diagram of the ICD 10 is shown in FIG. 2. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, the ICD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 may take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the heart rhythm employing any of the numerous signal processing methodologies known in the art. A tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, may be stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair may include any of the following exemplary combinations: any pair of defibrillation coil electrodes 8, 20 or 23; any of the defibrillation coil electrodes 8, 20 or 23 with housing 11; a tip electrode 17 or 26 with housing 11; a tip electrode 17 or 26 with a defibrillation coil electrode 20 or 23; or an atrial tip electrode 17 with ventricular ring electrode 24. While these electrode combinations are provided as examples of typically used far-field electrode pairs, the list is by no means exhaustive and extends to any combination of electrodes that provides a signal different from those used for obtaining near-field EGM signals. The use of near-field and far-field EGM sensing of arrhythmia episodes is described in U.S. Pat. No. 5,193,535, issued to Bardy, incorporated herein by reference in its entirety. Annotation of sensed events which may be displayed and stored with EGM data is described in U.S. Pat. No. 4,374,382 issued to Markowitz, incorporated herein by reference in its entirety.

Referring again to FIG. 2, the telemetry circuit 330 may receive downlink telemetry from and may send uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. In accordance with the present invention, EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated ROM in which stored programs controlling the operation of the microprocessor 224 reside. A portion of the random access memory 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067, 473 issued to Greeninger et al., incorporated herein by reference in its entirety. Right ventricular coil electrode 20 must be placed in the right ventricle in a position so that defibrillation therapies will have the greatest likelihood of bringing the heart out of ventricular defibrillation. It is also necessary to determine what voltage is necessary to end a ventricular fibrillation event. This voltage is called the defibrillation threshold.

The objectives of determining proper placement of the right ventricular coil electrode and the defibrillation threshold have been accomplished in the past by installing the right ventricular electrode in the patient's heart, inducing ventricular fibrillation, and trying to treat the defibrillation at various voltages and locations until the proper location for the right ventricular electrode and the defibrillation threshold are determined. The ventricular fibrillation may be induced by a pulsing of the right ventricular coil electrode 20 synchronized with the T-wave, by passing an alternating current through the heart, or by other means known in the art. It may also be induced by pulsing the ring electrode 24 or extendable helix electrode 26. Since the coil electrode has a much larger surface area from which the electrical charge may be dissipated, it is often preferable to induce fibrillation through one of the other electrodes.

The patient is under general anesthesia or is sedated but conscious throughout this procedure, but it is still a potentially traumatic and painful procedure, since the typical defibrillation pulse is 750 volts and several attempts may be required to determine proper lead placement and defibrillation threshold.

Embodiments of the present invention allow implantation of the right ventricular coil electrode and determination/estimation of the defibrillation threshold with fewer fibrillation/defibrillation cycles required. Some embodiments of the invention allow for the placement of the right ventricular coil electrode and estimation/determination of the defibrillation threshold without the need to put the patient's heart into ventricular fibrillation at all.

Certain embodiments of the invention involve methods of implanting the right ventricular lead in the patient's right ventricle. A pocket is prepared in the patient's chest and an ICD device housing is installed in this pocket. The device housing could be the actual ICD itself or a "dummy" housing used to simulate the location of the housing when the housing is used as an indifferent electrode. The dummy housing could also be an electrode pad taped to the skin over the intended location of the device. The device housing 11 may be used as a second or third electrode during embodiments of methods of the invention, as could coronary sinus defibrillation electrode 8 and the defibrillation electrode 23 located on the right atrial lead 6 and often installed in the superior vena cava. During the implantation of the right ventricular lead 16, a (series of) low voltage pulse(s) is delivered to the heart through the right ventricular lead 16. The pulse could be delivered by the ICD 10 itself through the pacer timing and control circuitry 212 to any of the defibrillation electrodes 8, 20, or 23. The pulse could also be delivered by an external stimulator attached to a defibrillation lead and a dummy housing, or by any means known in the art. The pulse could be any voltage, including but not limited to 1 to 10 volts. For safety reasons the pulse may be synchronized with the R-wave ventricular contraction to reduce or eliminate noticeable stimulation of the heart. When the pulse amplitude is selected to be lower than the cardiac stimulation threshold, the pulse frequency can be increased beyond the frequency of the heart, improving the feedback to the implanter. The pulse could also be applied through the right ventricular coil electrode 20 to minimize stimulation of the heart by spreading the pulse over the larger surface area of the coil electrode. Any electrode on the right ventricular lead 16 could, of course, deliver the pulse.

The low voltage pulse may then be measured on the patient's skin by an array of body surface potential measuring (BSP) electrodes affixed to the patient's body. The potential difference between the right ventricular defibrillation electrode and the defibrillator housing or a second defibrillation electrode generates a voltage gradient field in the human body that extends from the electrodes through the right and left ventricle of the heart towards the body surface. It is believed that a correlation exists between the voltage gradients in remote dorso-lateral areas of the left ventricle—which predominantly determine the defibrillation efficacy or defibrillation threshold—and the voltage gradients on the dorso-lateral body surface of the left thoracic wall. The voltage gradient field distribution is strongly related to position of the defibrillation electrode in the right ventricle. The basic concept is that maximization of voltage gradients on the skin—the Body Surface Potential gradients—in the dorso-lateral area of the left thoracic wall under the left scapula represents a maximization of voltage gradients in the left ventricle and thereby minimization of the voltage or energy required for effective defibrillation. The maximization of the BSP gradients can be obtained by optimizing the position and orientation of the defibrillation electrode in the right ventricle. In other words, it is believed that the optimal location of the right ventricular electrode corresponds with the location that results in the maximum absolute voltage gradient on a patient's back. This correlation is strongest when the measurement is taken under the left scapula at approximately the altitude of the left ventricle.

In addition, for instance, the right ventricular electrode is in the optimal position when the voltage gradient, as measured by the BSP electrodes, is maximized on the left side of the patient's body relative to the voltage gradient on the right side of the patient's body. In this situation the average BSP gradient can be measured by BSP electrodes located on the patient's lateral thorax wall and/or extremities such as arms and legs.

Figure 3:
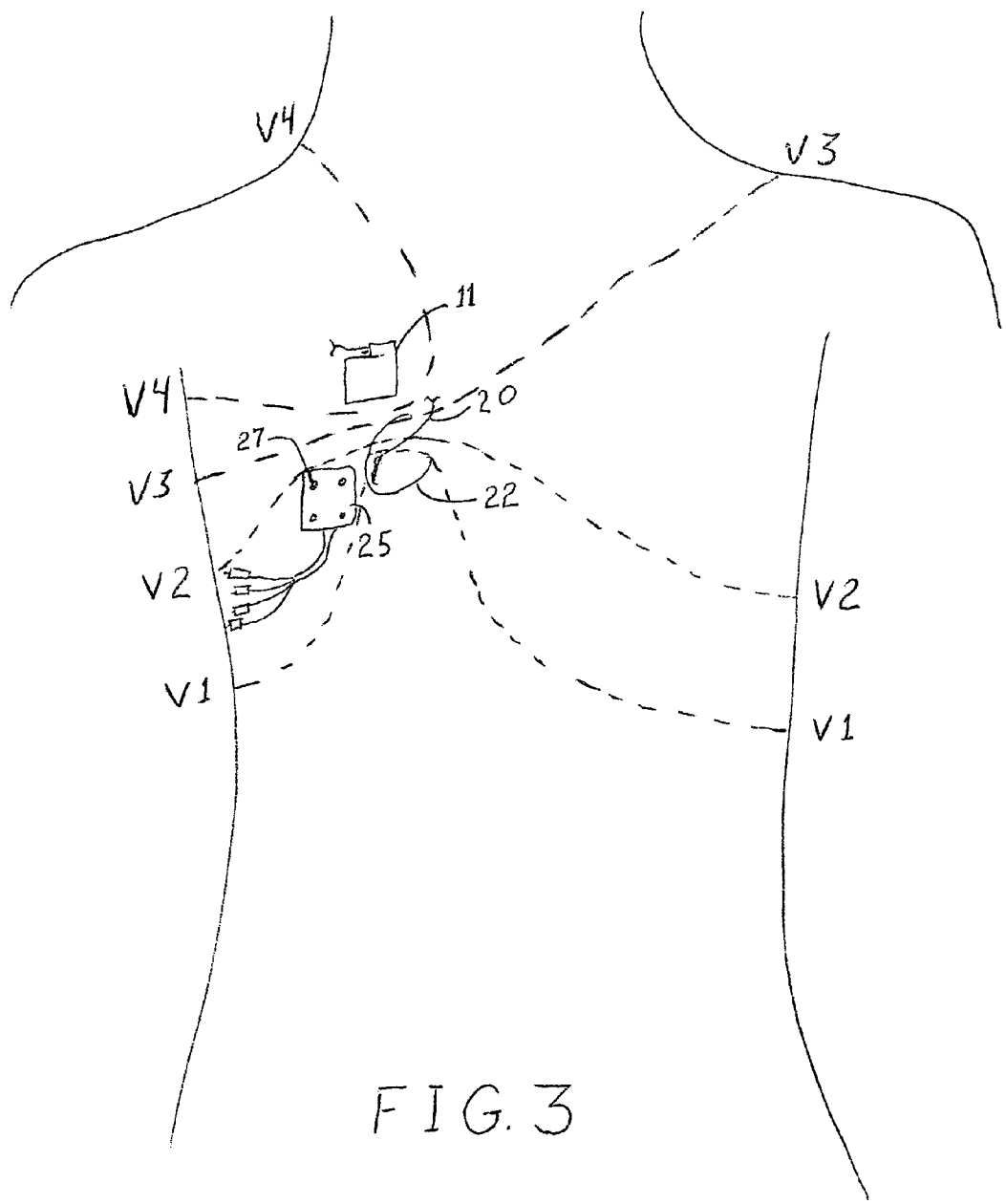
FIG. 3 is a rear schematic view of a patient with an implanted ICD in accordance with embodiments of the invention.

FIG. 3 is a rear schematic view of a patient with an ICD implanted. The right ventricular coil 20 is shown within the heart 22. The device housing 11 is shown as installed in the anterior pocket. A pad 25 of BSP electrodes 27 is attached to the back of the patient in an appropriate location. The pad 25 of BSP electrodes 27 may be adhered to the patient's body by medical adhesive or by any other means known in the art and may include any number of BSP electrodes. There may also be embodiments of the invention where more than one pad of BSP electrodes is used.

FIG. 3 also includes a representation of voltage gradients across the patient's body when the right ventricular electrode is implanted in the proper position. The lines V1 through V6 provide a general representation of isopotential lines at the patient's skin.

Figure 4:
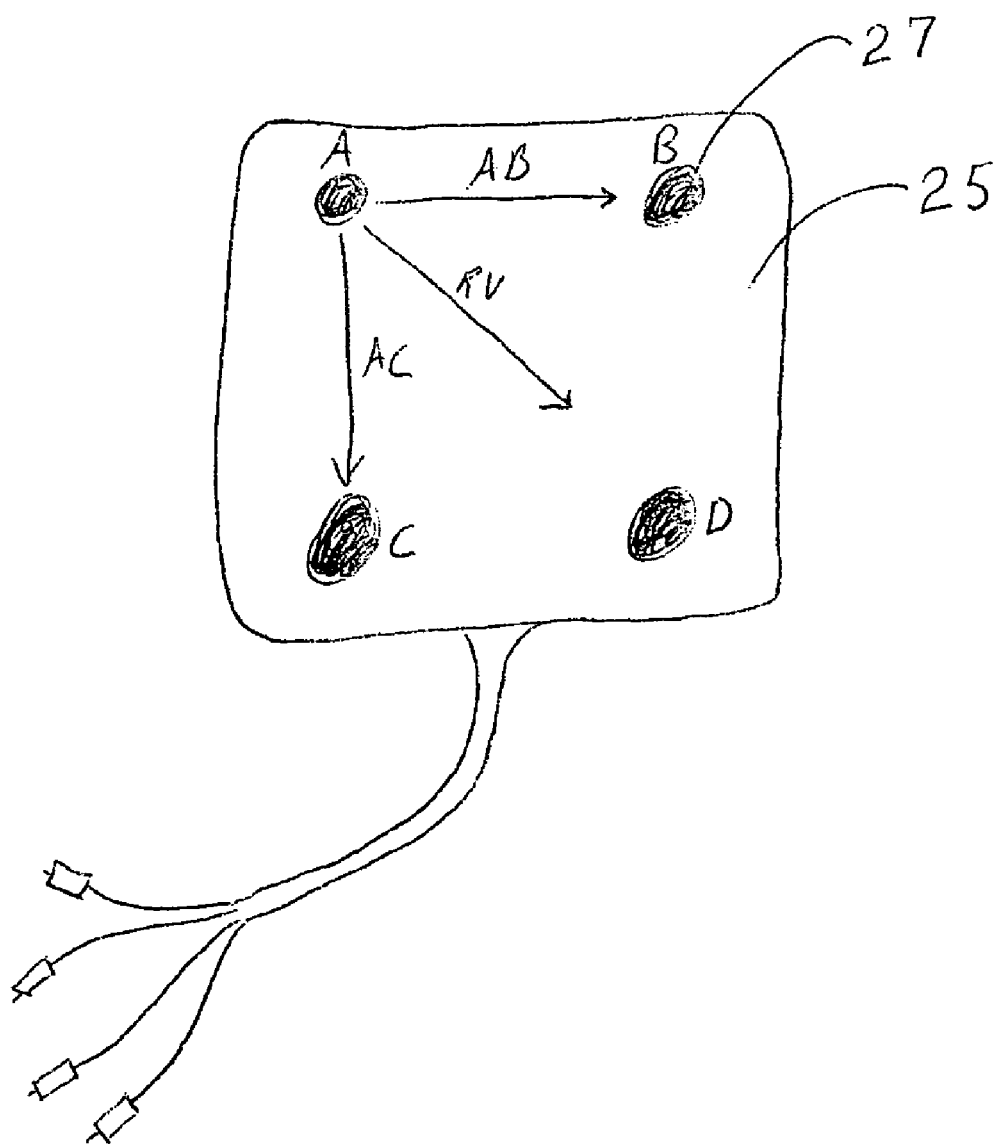
FIG. 4 is a plan view of a pad of BSP electrodes in accordance with an embodiment of the invention.

FIG. 4 is a plan view of a pad of BSP electrodes in accordance with an embodiment of the invention. The pad shown has four electrodes in a square configuration. The equidistant and perpendicular orientation of the electrodes relative to each other makes the calculation of the resultant surface potential vector very straightforward.

Using the BSP electrodes of the embodiment shown in FIG. 4 as an example, the absolute voltage gradient can be determined. It is referred to here as the absolute voltage gradient because the correlation with optimal right ventricular electrode placement is not necessarily related to the direction of the voltage gradient and mainly related to the absolute value or amplitude. The absolute value of the voltage gradient may be determined by finding the potential difference over a known distance in at least two directions. These potential differences are converted to measured vectors with identical units of measure ((potential difference)/distance) by dividing the gradient by the distance over which the gradient is measured. The amplitude of the vector resulting from the addition of the measured vectors, called here the resultant vector, can be calculated by adding the various vectors in a way that is well known in the art.

A pulse may be delivered in coordination with the R wave or, if below the pacing threshold, more frequently. The resultant vector amplitude may be calculated for each of these pulses and conveyed to the implanter of the device on an essentially real-time basis. This information may be conveyed to the implanter by way of a numerical value on a computer display, a audible signal with a frequency proportional to the resultant vector amplitude, an audible signal with a volume proportional to the resultant vector amplitude, a visual display with a color and/or intensity proportional to the resultant vector amplitude, a sensory signal with a vibration frequency proportional to the resultant vector amplitude, or any means known in the art to convey this information to the implanter of the electrode. In this way the implanter of the electrode may easily manipulate the electrode location until the maximum resultant vector amplitude is achieved.

In the embodiment of FIG. 4, the BSP electrodes 27 are labeled "A," "B," "C," and "D." A measured vector "AB" can be found by measuring the potential differential from A to B during a test pulse and dividing that differential by the distance from A to B. A second measured vector "AC" can be found by measuring the potential differential from A to C and dividing that differential by the distance from A to C. Since the pad 25 of the embodiment of FIG. 4 has four electrodes in a square configuration, the vectors AB and AC are perpendicular to each other. To calculate the amplitude of the resultant vector, one can use the Pythagorean theorem and simply take the square root of the sum of the squares of the measured vectors. The two measured vectors may also be taken from any two pairs of the electrodes, as long as one electrode is common to both vectors so as to be useful as a basis for the vector addition. Another embodiment allowing the use of the Pythagorean theorem is one of two pairs of electrodes with perpendicular interconnecting lines, which is the case for vectors AD and BC.

It may be desirable to determine the resultant vector amplitude from several points and average or otherwise compare or consolidate the results. For example, in addition to the measure vectors just described, one could determine measured vectors from electrode D to electrodes B and C respectively to determine vectors DB and DC. The resultant vector found by adding these two vectors will be within a reasonable margin of error to the vector found by the addition of AB and AC. There is no requirement that the measured vectors used in the embodiment shown in FIG. 4 be perpendicular to each other, and one of the measured vectors could be a diagonal vector across the pad 25. There is also no requirement that there be four electrodes on a pad. Three electrodes on a pad are sufficient to measure component vectors. As long as the distances between the electrodes and the orientation of the measured vectors are known and the component vectors are not parallel, a resultant vector amplitude can be calculated.

When after collecting ample clinical information on this method, the direction of the resultant BSP gradient vector shows to be reproducible with only small deviations, the BSP gradient can be measured by placing two BSP electrodes on the skin with the interconnecting line parallel to the BSP gradient vector. Taking the angle between the actual BSP gradient vector and the component vector between both BSP electrodes is equal to alpha, than the actual BSP gradient amplitude can be written as:

a. BSP gradient amplitude =(voltage difference between BSP electrodes)/(distance between BSP electrodes) * cosine(alpha)

For small angles of alpha, the cosine of (alpha) is approximately equal to 1 (for alpha =10 degrees, the error is about 1.5%).

The advantage of using a pad with 3 BSP electrodes in a triangular fashion (preferably with equal distances) or 4 BSP electrodes (preferably in a square pattern) is that the measured and calculated resultant BSP vector amplitude and direction are independent of the orientation at which the pad is placed on the skin.

The pad of FIG. 4 can be connected to a monitoring computer used during the implantation procedure and the amplitude of the resultant vector can be continuously updated as each pulse results in new measured BSPs based on the location of the right ventricular electrode. The installer of the right ventricular electrode simply has to move the electrode within the right ventricle until the maximum resultant vector amplitude is found.

Once the optimal right ventricular lead position is determined, the DFT may be accurately estimated by assuming that the gradient in the left ventricle is proportional to the resultant vector on the skin. Because a fixed voltage gradient is necessary to depolarize vascular tissue, the voltage needed to overcome the defibrillation threshold is inversely proportional to the amplitude of the resultant vector. Therefore the energy needed to defibrillate the heart, or the DFT, is inversely proportional to the square of the resultant vector amplitude (RVA). For example, if the optimization of the right ventricular coil position results in an increase in the resultant vector amplitude of 20%, the DFT would be reduced by approximately 30%.

$$DFT=(1/RVA)^2=(1/1.2)^2=1/1.44=0.69$$

By using the additional information provided by the resultant vector amplitude and means known in the art for estimating DFT, a DFT may be estimated more quickly with no need, or at least a lesser need, to put the patient's heart into defibrillation and administer defibrillation therapy to determine DFT.

Defibrillation threshold, determined with a defibrillation test protocol, is not very reproducible. Repeating the defibrillation test protocol in the same patient under the same conditions usually results in a different value of the DFT. Clinical studies have shown that the correlation between the first and second measured DFT of a patient group had a correlation of about r=0.5. Therefore it is theorized that the body surface potential gradient measured on a representative region of the left dorsal or dorso-lateral thorax has a stronger correlation to the DFT of the patient than the DFT to itself. Therefore the BSP measurement can be considered as good as the DFT measurement itself.

The correlation between the BSP gradient can be further refined by taking some gross anatomical factors into consideration. The BSP gradient decays with distance to the defibrillation electrode interconnecting line. The chest circumference could serve as a linear factor for estimating the effective BSP gradient: the larger the thorax circumference, the larger the decay of the voltage gradient and the lower the BSP. The effective BSP can be calculated as the measured BSP multiplied with the chest circumference and divided by a standard chest circumference.

Another correction factor could be the ratio between the maximum distance between the middle of the Right Ventricular electrode and any left ventricular tissue and the distance between the middle of the RV electrode to the center of the BSP pad. In a linear approach the DFT is inversely proportional to said ratio.

Despite the uncertainties in assessing individual defibrillation threshold due to its stochastic nature, the lowest defibrillation threshold is likely to be obtained when the BSP gradient is maximized, without the use of any correction factors. This underlines the usefulness of the invention.

Aspects of the present invention, which allow prediction of defibrillation threshold, can save a physician considerable time and, moreover; prevent unnecessary discomfort to the patient. Once the proper right ventricular electrode position is identified, simple determination of the defibrillation threshold may be made with no or very few therapies needing to be delivered to the patient. Repeated delivery of unnecessary defibrillation therapies to determine defibrillation efficacy may be avoided.

Thus, embodiments of the Implantation of Medical Device with Measurement of Body Surface Potential are disclosed. The disclosed embodiments are presented for purposes of illustration and not limitation, and the scope of the present application is limited only by the claims that follow.

What is claimed is:

1. A method of implanting at least one lead for a cardio defibrillator, comprising:
   a. installing a RV defibrillation electrode in a right ventricle of a patient's heart;
   b. installing a second defibrillation electrode in the patient;
   c. attaching at least three body surface potential (BSP) electrodes capable of measuring body surface potential to the patient's skin;
   d. creating a potential difference between the RV defibrillation electrode and the second defibrillation electrode;
   e. measuring the body surface potential at the at least three body surface potential (BSP) electrodes caused by the potential difference between the defibrillation electrodes;
   f. determining the amplitude of a resultant vector formed by the measured potential differences between the at least three body surface potential (BSP) electrodes, the measured potential differences between the at least three body surface potential (BSP) electrodes forming component vectors of the resultant vector; and
   g. manipulating the location of at least one of the defibrillation electrodes to increase the amplitude of the resultant vector formed by the measured potential differences between the at least three body surface potential (BSP) electrodes.

2. The method of claim 1, wherein the at least three body surface potential (BSP) electrodes are four body surface potential (BSP) electrodes.

3. The method of claim 1, wherein the at least three body surface potential (BSP) electrodes are supported together on a single pad.

4. The method of claim 2, further including positioning the pad on the patient's back below the left scapula.

5. The method of claim 1, wherein the second defibrillation electrode comprises at least one of a housing for an implantable cardio defibrillator and a superior vena cava electrode.

6. The method of claim 1, wherein the potential difference between the RV defibrillation electrode and the second defibrillation electrode is between about 1 to 10 volts.

7. The method of claim 1, wherein the potential difference between the RV defibrillation electrode and the second defibrillation electrode is below the pacing threshold of the patient's heart.

8. The method of claim 1, including the step of providing a variable signal proportional to the amplitude of the resultant vector selected from the group consisting of a variable frequency audio signal, a variable color visual signal, and a variable frequency vibration sensory signal.

9. The method of claim 1, wherein the at least one manipulated defibrillation electrode is fixed in the location that provides the relative maximum amplitude of the resultant vector.

10. A method of implanting at least one lead for a cardio defibrillator, comprising:
    a. installing a RV defibrillation electrode in a right ventricle of a patient's heart;
    b. installing a second and a third defibrillation electrode in the patient;
    c. attaching at least three body surface potential (BSP) electrodes capable of measuring body surface potential to the patient's skin;
    d. creating a potential difference between the RV defibrillation electrode and the second defibrillation electrode;
    e. measuring the body surface potential at the at least three body surface potential (BSP) electrodes caused by the potential difference between the defibrillation electrodes;
    f. determining the amplitude of a resultant vector formed by the measured potential differences between the at least three body surface potential (BSP) electrodes, the measured potential differences between the at least three body surface potential (BSP) electrodes forming component vectors of the resultant vector; and
    g. creating a potential difference between the RV defibrillation electrode and the third defibrillation electrode to determine if such potential difference increases the amplitude of the resultant vector formed by the measured potential differences between the at least three body surface potential (BSP) electrodes.

11. The method of claim 10, wherein the at least three body surface potential (BSP) electrodes are four body surface potential (BSP) electrodes arranged in a generally rectangular configuration and supported on a single adhesive pad.

12. The method of claim 11, wherein the component vectors are two component vectors, and the component vectors are formed by subtracting the measured potential of the body surface potential (BSP) electrodes at opposite diagonal corners.

13. The method of claim 12, wherein each component vector is formed by dividing out distance between the body surface potential (BSP) electrodes forming the respective component vector.

14. The method of claim 10, wherein the potential differences created between the defibrillation electrodes are synchronized to an R-wave of the patient's heart.

15. The method of claim 10, wherein the potential differences created between the defibrillation electrodes are below the patient's pacing threshold.

16. The method of claim 10, wherein the resultant vector amplitude is corrected by applying correction factors based on thoracic circumference and heart size.

* * * * *